US007643155B2

(12) United States Patent
Marks et al.

(10) Patent No.: US 7,643,155 B2
(45) Date of Patent: Jan. 5, 2010

(54) PARTIALLY COHERENT ILLUMINATION FOR INVERSE SCATTERING FULL-FIELD INTERFEROMETRIC SYNTHETIC APERTURE MICROSCOPY

(75) Inventors: Daniel L. Marks, Urbana, IL (US); Brynmor J. Davis, Champaign, IL (US); Stephen A. Boppart, Champaign, IL (US); Paul Scott Carney, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 12/131,390

(22) Filed: Jun. 2, 2008

(65) Prior Publication Data

US 2009/0086216 A1 Apr. 2, 2009

Related U.S. Application Data

(63) Continuation-in-part of application No. 11/775,572, filed on Jul. 10, 2007, now Pat. No. 7,602,501.

(60) Provisional application No. 60/819,593, filed on Jul. 10, 2006.

(51) Int. Cl.
*G01B 11/02* (2006.01)
(52) U.S. Cl. ..................................... 356/497
(58) Field of Classification Search ............. 356/497, 356/479
See application file for complete search history.

(56) References Cited

U.S. PATENT DOCUMENTS 5,975,697 A * 11/1999 Podoleanu et al. .......... 351/206

OTHER PUBLICATIONS

Demonstrations of Inverse Scattering in Optical Coherence Tomography, Proceedings of the SPIE, vol. 6079, pp. 60791T-60791T-9, Feb. 2006.*
Carney "*ECE 569: Lecture* 15", Department of Electrical and Computer Engineering, University of Illinois at Urbana Champaign, Urbana, IL, 2004.

(Continued)

*Primary Examiner*—Tarifur Chowdhury
*Assistant Examiner*—Jonathon D Cook
(74) *Attorney, Agent, or Firm*—Sunstein Kann Murphy & Timbers LLP

(57) ABSTRACT

Methods and apparatus for three-dimensional imaging of a sample. A source is provided of a beam of light characterized by partial spatial coherence. The beam is focused onto a sample and scattered light from the sample is superposed with a reference beam derived from the source onto a focal plane detector array to provide an interference signal. A forward scattering model is derived relating measurement data to structure of an object to allow solutions of an inverse scattering problem, based upon the interference signal so that a three-dimensional structure of the same may be inferred. The partial spatial coherence of the source, which may be fixed or variable, may advantageously provide for rejection of multiple scattering artifacts and thus improve image quality.

10 Claims, 4 Drawing Sheets

OTHER PUBLICATIONS

Davis et al. "*Autocorrelation artifacts in optical coherence tomography and interferometric synthetic aperture microscopy*", Optics Letters, vol. 32, No. 11, pp. 1441-1443, Jun. 1, 2007.

Yasuno et al. "*Non-iterative numerical method for laterally, supersolving Fourier domain optical coherence tomography*", Optics Express, vol. 14, No. 9, pp. 1006-1020, Sep. 2007,.

Davis et al. "*Nonparaxial vector-field modeling of topical coherence tomography and interferometric synthetic aperture microscopy*", J. Opt. Soc. Am. A, vol. 24, No. 9, pp. 2527-2542, Sep. 2007.

Ralston et al. "*Inverse scattering for optical coherence tomography*", J. Opt. Soc. Am. A, vol. 23, No. 5, pp. 1027-1037, May 2006.

Ralston et al. "*Demonstration of inverse scattering in optical coherence tomography*", Proceeding of the SPIE, vol. 6079, pp. 60791T-1-60791T-9, Feb. 20, 2006.

Ralston et al. "*Deconvolution Methods for Mitigation of Transverse Blurring in Optical Coherence Tomography*", IEEE Transactions on Image Processing, vol. 14, No. 9, pp. 1254-1264, Sep., 2005.

Bruno & Chaubell "*One-dimensional inverse scattering problem for optical coherence tomography*", Institute of Physics Publishing; Inverse Problems, vol. 21, pp. 499-524, Feb. 23, 2005.

Choma et al. "*Sensitivity advantage of swept source and Fourier domain optical coherence tomography*", Optics Express, vol. 11, No. 18, pp. 2183-2189, Sept. 8, 2003.

Ralston et al. "*Inverse scattering for high-resolution interferometric microscopy*", Optics Letters, vol. 31, No. 24, pp. 3585-3587, Dec. 15, 2006.

Ralston et al. "*Real-time interferometric synthetic aperture microscopy*", Optics Express, vol. 16, No. 4, pp. 2555-2569, Feb. 18, 2008.

Grieve et al. "*In vivo anterior segment imaging in the rat eye with high speed white light full-field optical coherence tomography*", Optics Express, vol. 13, No. 16, pp. 6286-6295, Aug. 8, 2005.

Marks et al. "*Inverse scattering for rotationally scanned optical coherence tomography*", J. Opt. Soc. Am. A, vol. 23, No. 10, pp. 2433-2439, Oct. 2006.

Marks et al. "*Inverse scattering for frequency-scanned full-field optical coherence tomography*", J. Opt. Soc. Am. A, vol. 24, No. 4, pp. 1034-1041, Apr. 2007.

Ralston et al. "Interferometric synthetic aperture microscopy", Nature Physics, vol. 3, pp. 129-134, Feb. 2007.

Akiba et al. "*Full-field optical coherence tomography by two-dimensional heterodyne detection with a pair of Ccd cameras*", Optics Letters, vol. 28, No. 10, pp. 816-818, May 15, 2003.

Beaurepaire et al. "*Full-field optical coherence microscopy*", Optics Letters, vol. 23, No. 4, pp. 244-246, Feb. 15, 1998.

Blazkiewicz et al. "*Signal-to-noise ratio study off full-field Fourier-domain optical coherence tomography*", Applied Optics, vol. 44, No. 36, pp. 7722-7729, Dec. 20, 2005.

Dubois et al. "*High-resolution full-field optical coherence tomography with a Linnik microscope*", Appl. Opt., vol. 41, No. 4, pp. 805-812, Feb. 1, 2002.

Dubois et al. "*Three-dimensional cellular-level imaging using full-field optical coherence tomography*", Phys. Med. Biol., vol. 49, pp. 1227-1234, Mar. 18, 2004.

Dubois et al. "*Ultrahigh-resolution full-field optical coherence tomography*"; Appl. Opt., vol. 43, No. 14, pp. 2874-2883, May 10, 2004.

Laude et al. "*Full-field optical coherence tomography with thermal light*", Appl. Opt., vol. 41, No. 31, pp. 6637-6645, Nov. 1, 2002.

Moneron et al. "*Stroboscopic ultrahigh-resolution full-field optical coherence tomography*", Optics Letters, vol. 30, No. 11, pp. 1351-1353, Jun. 1, 2005.

Moreau et al. "*Full-field birefringence imaging by thermal-light polarization-sensitive optical coherence tomography. Ii. Instrument and results*", Appl. Opt., vol. 42, No. 19, pp. 3811-3818, Jul. 1, 2003.

Watanabe et al. "*Full-field optical coherence tomography by achromatic phase shifting with a rotating polarizer*", Appl. Opt., vol. 44, No. 8, pp. 1387-1392, Mar. 10, 2005.

Zvyagin, A. "*Fourier-domain optical coherence tomography: optimization of signal-to-noise ratio in full space*", Opt. Comm., vol. 242, pp. 97-108, 2004.

Zvyagin et al. "*Image reconstruction in full-field Fourier-domain optical coherence tomography*", J. Opt. A: Pure Appl. Opt., vol. 7, pp. 350-356, Jun. 21, 2005.

Považay et al. "*Full-field time-encoded frequency-domain optical coherence tomography*", Optics Express, vol. 14, No. 17, pp. 7661-7669, Aug. 21, 2006.

\* cited by examiner

PARTIALLY COHERENT ILLUMINATION FOR INVERSE SCATTERING FULL-FIELD INTERFEROMETRIC SYNTHETIC APERTURE MICROSCOPY

The present application is a continuation-in-part of U.S. Patent Application Ser. No. 11/775,572, filed Jul. 10, 2007, and, like that application, claims the priority of U.S. Provisional Patent Application Ser. No. 60/819,593, filed Jul. 10, 2006. Both of these applications are incorporated herein by reference in their entirety.

This invention was developed with Government support under Grant Nos. IR21-EB005321 and IR01-EB005221, awarded by the National Institutes of Health and CAREER Awards BES 03-47747, BES 05-19920, BES 06-19257 and 0239265, awarded by the National Science Foundation. The Government has certain rights in the invention.

TECHNICAL FIELD OF THE INVENTION

The present invention pertains to methods and apparatus for computed imaging of an object on the basis of partially coherent illumination of the object and reconstruction of the three-dimensional susceptibility of the object from analysis of scattering detected therefrom.

BACKGROUND OF THE INVENTION

Interferometric synthetic aperture microscopy (ISAM) is a method of tomographic optical microscopy that brings the power of computed imaging and inverse scattering together with interferometric broadband optical imaging. ISAM provides spatially invariant resolution of objects in an extended 3-D volume including regions away from the focus of the objective and quantitative estimation of the inhomogeneities in refractive index or susceptibility of an object. The solution of the inverse problem for ISAM has been found for many scanning geometries and types of illumination, including low-numerical aperture scanned-beam (see Ralston et al. "Inverse scattering for optical coherence tomography," *J. Opt. Soc. Am. A*, 23, pp. 1027-37 (2006), hereinafter Ralston (2006)), high numerical aperture scanned-beam (see Ralston et al., "Inverse scattering for high-resolution interferometric microscopy," *Opt. Lett.*, 31, pp. 3585-87 (2006), hereinafter Ralston (2006a)), rotationally-scanned beam catheter (see Marks et al., "Inverse scattering for rotationally scanned optical coherence tomography," *J. Opt. Soc. Am. A*, 23, pp. 2433-39 (2006)), and full-field illumination (see Marks et al., "Inverse scattering for frequency-scanned full-field optical coherence tomography," *J. Opt. Soc. Am. A*, 24, pp. 1034-41 (2007)). The latter reference will be referred to hereinafter as Marks (2007), and all of the foregoing articles are incorporated herein by reference.

In prior treatments, while the illumination source may be temporally incoherent, or broadband, a spatially coherent (single mode) illumination source was assumed. In general, however, illumination sources in microscopy are, in fact, spatially partially coherent, as discussed, for example, in Mandel & Wolf, *Optical Coherence and Quantum Optics*, (Cambridge University Press, 1995), which is incorporated herein by reference. Solutions derived in prior treatments that assumed a single spatial mode are thus inapplicable to the case of illumination by partially coherent sources.

SUMMARY OF THE INVENTION

In accordance with preferred embodiments of the present invention, a synthetic aperture microscope is provided that has a source of illumination characterized by a degree of partial spatial coherence for illuminating a sample. Additionally, the synthetic aperture microscope has a sensor for detecting a field of light scattered by the sample, as well as a processor for deconvolving the field at the sensor to recover a three-dimensional image of the sample.

In accordance with other embodiments of the invention, the synthetic aperture microscope may also have a reference arm for relaying a portion of the illumination onto the sensor. The source of illumination may include an aperture, which may be variable, and, more particularly, the source of illumination may include an iris. Additionally, the reference arm includes a reference delay mirror.

In accordance with another aspect of the invention, a method is provided for determining a three-dimensional susceptibility of a sample. The method has steps of:
  a. illuminating the sample with partially coherent light derived from a source;
  b. superposing scattered radiation from the sample with a reference beam derived from the source, using optics characterized by a focus and a Rayleigh range, to provide a detector signal at a detector; and
  c. solving an inverse scattering problem based upon the detector signal to infer a three-dimensional susceptibility of the sample.

The method may also have a step of varying the spatial coherence of the source, and a step of disposing the sample at a distance from the focus that exceeds the Rayleigh range. A further step may include spectrally resolving the detected light.

The foregoing step of solving the inverse scattering problem may include solving a least squares problem relative to a forward scattering model and may include solving a resampling problem.

In accordance with yet another aspect of the invention, a computer program product is provided for use on a computer system for determining a three-dimensional susceptibility of a sample. The computer program product has a computer usable medium with computer readable program code thereon, the computer readable program code including:
  a. program code for generating a forward scattering model based on forward scattering of partially coherent light by a point source;
  b. program code for receiving a signal based on coherent detection of scattering from the sample; and
  c. program code for solving an inverse scattering problem based upon the detector signal to infer a three-dimensional susceptibility of the sample based on comparing the detected signal to data predicted from the forward scattering model.

DESCRIPTION OF THE FIGURES

The foregoing features of the invention will be more readily understood by reference to the following detailed description, taken with reference to the accompanying drawings, in which.

The reference-arm optics image the source plane on to the detector, so, in this simplified diagram, the source and detector planes are colocated.

DESCRIPTION OF SPECIFIC EMBODIMENTS OF THE INVENTION

Figure 1:
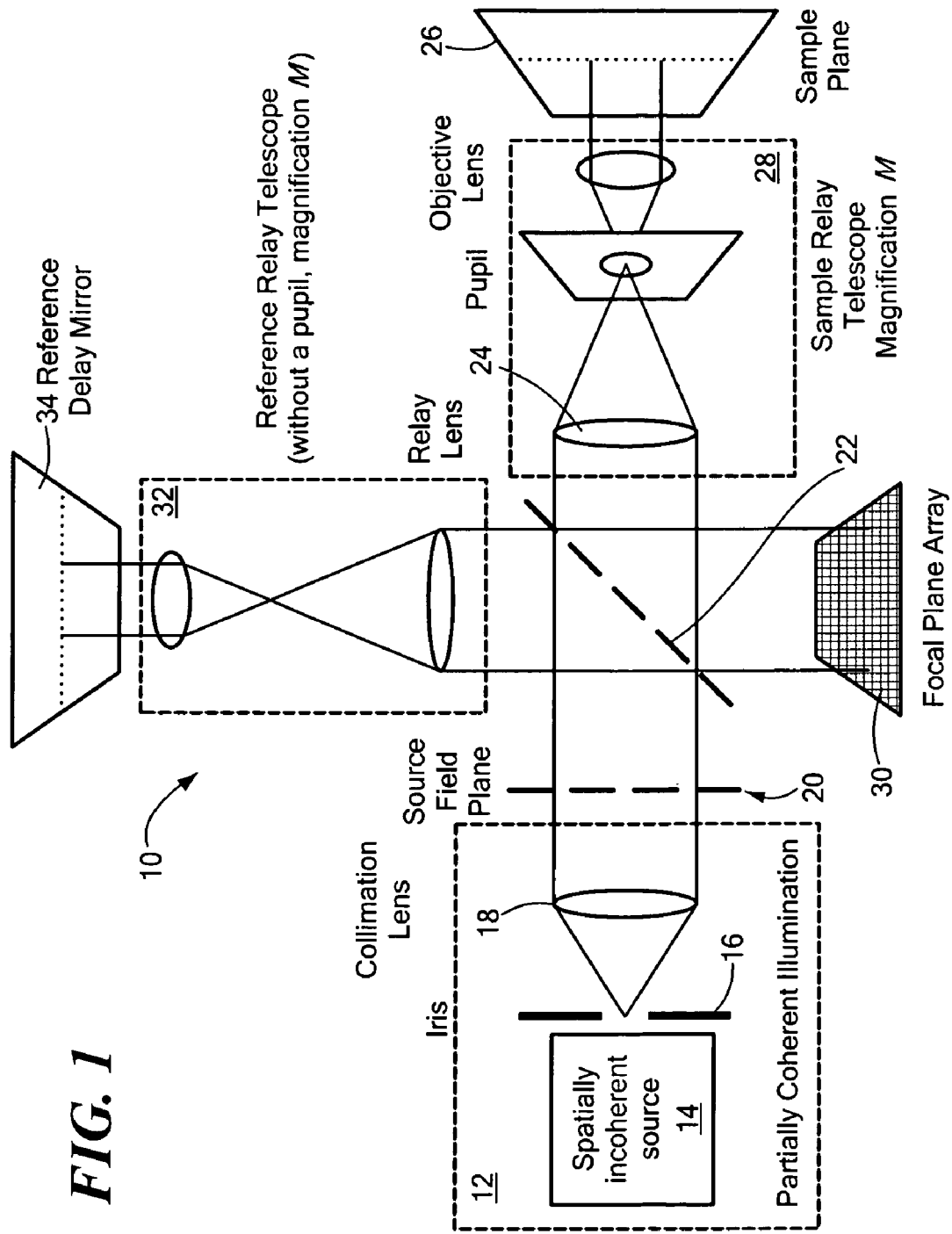
FIG. 1 is a schematic depiction of a full-field optical coherence tomography instrument with a source of adjustable partial coherence, in accordance with an embodiment of the present invention.

In accordance with the present invention, the solution of the inverse scattering problem for cases using partially coherent illumination sources is derived for data available in applications utilizing the instrumentation either of full-field optical coherence tomography (OCT) or of optical coherence microscopy (OCM).

As used herein and in any appended claims, the term "image," used as a noun or as a verb, and unless otherwise required by context, refers to the creation of a holomorphic mapping of values characterizing points in a space such that the values may, thereafter, be associated, one-to-one, with particular points in the space. The values may be stored in a memory, or displayed on a monitor, or fixed in a medium. The values mapped in the creation of an image are typically scalar, such as the scalar susceptibility associated with each point in the volume of the imaged sample. However, the mapping of a vector (or tensor) property of the sample, whether in two or three dimensions, and whether also incorporating other dimensions such as frequency or time (or some other experimental value, such as temperature, for that matter), will also be considered "imaging" for purposes of the following description and claims.

As used herein and in any appended claims, the term "deconvolve" is used in a general sense to encompass any resolution of a scatter image to mathematically reconstitute the structure that gave rise to it, and is not limited to the inverse of a convolution operation, unless so specified in context.

Other references describing OCT or OCM embodiments, that are, similarly, incorporated herein by reference, include the following:

T. S. Ralston, D. L. Marks, P. S. Carney, and S. A. Boppart, "Interferometric synthetic aperture microscopy," Nat. Phys., vol. 5, pp. 129-34, 2007, hereinafter, Ralston, 2007.

M. Akiba, K. P. Chan, and N. Tanno, "Full-field optical coherence tomography by two-dimensional heterodyne detection with a pair of CCD cameras," Opt. Lett., vol. 28, pp. 816-18, 2003.

E. Beaurepaire and A.-C. Boccara, "Full-field optical coherence microscopy," Opt. Lett., vol. 23, pp. 244-46, 1998.

P. Blazkiewicz, M. Gourlay, J. R. Tucker, A. D. Rakic, and A. V. Zvyagin, "Signal-to-noise ratio study of full-field Fourier-domain optical coherence tomography," Appl. Opt., vol. 34, pp. 7722-29, 2005.

A. Dubois, L. Vabre, A.-C. Boccara, and E. Beaurepaire, "High-resolution full-field optical coherence tomography with a Linnik microscope," Appl. Opt., vol. 41, pp. 805-12, 2002.

A. Dubois, G. Moneron, K. Grieve, and A.-C. Boccara, "Three-dimensional cellular-level imaging using full-field optical coherence tomography," Phys. Med. Biol., vol. 49, pp. 1227-34, 2004.

A. Dubois, K. Grieve, G. Moneron, R. Lecaque, L. Vabre, and C. Boccara, "Ultrahigh-resolution full-field optical coherence tomography," Appl. Opt., vol. 43, pp. 2874-83, 2004.

K. Grieve, A. Dubois, M. Simonutti, M. Paques, J. Sahel, J.-E Le Gargasson, and C. Bocarra, "In vivo anterior segment imaging in the rat eye with high speed white light full-field optical coherence tomography," Opt. Expr., vol. 13, pp. 6286-95, 2005.

K. Grieve, G. Moneron, A. Dubois, J.-E Le Gargasson, and C. Boccara, "Ultrahigh resolution ex-vivo ocular imaging using ultrashort acquisition time en face optical coherence tomography," J. Opt. A, vol. 7, pp. 368-373, 2005.

B. Laude, A. De Martino, B. Drevillon, L. Benattar, and L. Schwartz, "Full-field optical coherence tomography with thermal light," Appl. Opt., vol. 41, pp. 6637-45, 2002.

G. Moneron, A.-C. Bocarra, and A. Dubois, "Stroboscopic ultrahigh-resolution full-field optical coherence tomography," Opt. Lett., vol. 30, pp. 1351-53, 2005.

J. Moreau, V. Lorlette, and A.-C. Bocarra, "Full-field birefringence imaging by thermal-light polarization-sensitive optical coherence tomography. II. instrument and results," Appl. Opt., vol. 42, pp. 3811-18, 2003.

Y. Watanabe, Y. Hayasaka, M. Sato, and N. Tanno, "Full-field optical coherence tomography by achromatic phase shifting with a rotating polarizer," Appl. Opt., vol. 44, pp. 1387-92, 2005.

A. V. Zvyagin, "Fourier-domain optical coherence tomography: optimization of signal-to-noise ratio in full space," Opt. Comm., vol. 242, pp. 97-108, 2004.

A. V. Zvyagin, P. Blazkiewicz, and J. Vintrou, "Image reconstruction in full-field Fourier-domain optical coherence tomography," J. Opt. A, vol. 7, pp. 350-56, 2005.

B. Povazay, A. Unterhuber, B. Hermann, H. Sattmann, H. Arthaber, and W. Drexler, "Full-field time-encoded frequency-domain optical coherence tomography," Opt. Express, vol. 14, pp. 7661-69, 2006.

In conventional OCM and OCT, the properties of illumination coherence may be manipulated to suppress or enhance various interference phenomena.

In particular, decreasing the spatial coherence of the source reduces the interference signal produced by multiply-scattered light. Because images are formed in OCT primarily from the singly-backscattered signal, the multiply-scattered light can contribute unwanted distortion and noise to be resulting image, as has been discussed by various investigators. In general, the solution of the inverse scattering problem for interferometric full-field microscopy depends on the spatial coherence of the illumination source. In a previously published paper, a solution of the inverse scattering problem was derived for the case of a fully coherent source and therefore is not applicable to the case of partially coherent illumination.

As will be made apparent through simulation as described in detail below, the use of partially coherent sources offers certain advantages.

Preferred embodiments of the present invention are described with reference to FIG. 1, wherein is depicted one particular embodiment of the invention in which a full-field interferometric microscope is employed under conditions of partially coherent illumination. This instrument is a full-field interferometric microscope, designated generally by numeral 10, with a module of varying spatial coherence, designated generally by numeral 12. Reference is made to the description of FIG. 3(a) in U.S. patent application Ser. No. 11/775,572 for explication of the other components of the full-field interferometric microscope. If the source 12 is set to be spatially coherent, then the setup is similar in operation to the instruments of earlier studies.

The illumination source 12 is diagrammed in the portion of FIG. 1 denoted by "partially coherent illumination." The illumination consists of a spatially incoherent primary source 14, an iris 16 placed in front of the primary source 14 to vary the apparent size of the source, and a collimation lens to collimate the source illumination. The iris is an example of an aperture limiting the dimensions of the spatially incoherent source as viewed from the sample, and the term "iris" is used in this Description, but without limitation, and any other partially coherent source may be employed within the scope of the present invention.

As used herein and in any appended claims, the term "spatially incoherent" as applied to a source of illumination refers to the fact that the electromagnetic field associated with different parts of the emitting surface of the source produce mutually incoherent electromagnetic fields, and do not interfere when averaged over an experimentally pertinent time scale such as the inverse bandwidth of the detection system.

An example of a spatially incoherent source is the filament of an incandescent light bulb. The spatially incoherent source may be a source of visible or infrared light, however the scope of the present invention is not so limited, and other sources of incoherent radiation, whether electromagnetic or otherwise (such as low-energy electron beams), are within the scope of the present invention, including instances in which the radiation may be characterized as a solution to a wave or a Helmholtz equation. In the case of an incandescent source, each point on the filament surface radiates a randomly fluctuating electromagnetic field, such that the fields radiated by different regions on the filament surface do not interfere when averaged over a long time interval. Another such source is a spatially coherent monochromatic laser, with its spatial coherence destroyed by a spinning or translating diffuser, as described, for example, by Goodman, Statistical Optics, (Wiley, 1985), which is incorporated herein by reference. Such a source produces quasi-monochromatic, spatially incoherent light. The light emanating from points on the incoherent source surface is collimated by the collimation lens so that the radiating source points produce mutually incoherent plane waves. Such illumination is akin to Koehler illumination, as described by Born & Wolf, *Principles of Optics*, (Cambridge Univ. Press, 1980) (incorporated herein by reference), in a conventional microscope, in contrast to critical illumination when the incoherent source surface is imaged onto the sample. By adjusting the size of the iris 16, the spatial coherence can be varied from very low (when the iris is opened), to very high (when the iris is closed). Specifically, there is a 2-dimensional Fourier transform relationship between the cross-spectral density at the field plane and the transmittance of the iris.

It is to be understood that within the scope of the present invention, the degree of spatial coherence may be set, or may be varied during the course of an experiment or measurement procedure.

The interferometer portion is now further described with reference to the schematic diagram shown in FIG. 1. The incoherent source 14, iris 16, and collimation lens 18 comprise an example of the partially coherent illumination system 12 that produces an adjustable partially coherent illumination at the source field plane 20. The interferometer itself is of a Michelson type and consists of reference and sample paths. A 50/50 beam splitter 22 divides the illumination field between these paths. As shown in FIG. (1), both the reference and sample fields are demagnified by telescopes of magnification factor M. In the sample relay telescope, a pupil 24 limits the spatial bandwidth of the field collected from the sample. The sample relay telescope afocally and telecentrically relays the field from the source field plane 20 to the sample plane 26 with demagnification. The sample plane corresponds to the front surface of the sample. The sample scatters the field backwards through the sample relay telescope 28, where it reflects off of the beam splitter and onto a focal plane array 30. The focal plane array 30 is placed so that the sample relay telescope 28 afocally and telecentrically images the sample plane to the focal plane array. The reference beam begins at the beamsplitter and is relayed by the reference delay telescope 32 to the reference delay mirror 34. The reference delay telescope afocally and telecentrically images the source field plane to the reference mirror plane. The field that reflects off the mirror is imaged afocally and telecentrically onto the focal plane array 30. The intensity of the interference pattern produced by the superimposed reference and sample signals is converted to a signal by the focal plane array. In practice, a Fizeau type interferometer where the reference beam is returned from a reflective planar surface placed in front of the sample avoids the need for a separate reference telescope to relay the reference field. The focal plane array detector signal, in turn, is processed by a inverse scattering solver, as described below, in order to allow reconstruction of the susceptibility of distinct points associated with the volume of the sample. The inverse scattering solver is a specialized processor, programmed to perform the steps of reconstruction of the scatterer as described in the following sections.

Incoherent source 14 of the instrument is preferably a spatially incoherent, quasimonochromatic source, and may be characterized by a tunable temporal frequency (or, equivalently, wavelength). Data are acquired by tuning the wavelength of the source over a particular bandwidth while recording the intensity of interferograms on the focal plane array. From these interferograms, the susceptibility of the sample is inferred.

In the following section, a general forward model is derived that is applicable to partially coherent full-field OCT. This general forward model will serve as the basis for partially coherent ISAM. In subsequent sections, the limit of fully incoherent illumination, and then partially coherent illumination, are treated, A linear solution for the inverse scattering problem for partially coherent illumination is derived. Finally, a simulation is presented where the solution of the inverse scattering problem is used to reconstruct the refractive index homogeneities of a sample consisting of point sources illuminated by a source of varying partial coherence.

The General Case

The objective in formulating the forward problem is to derive an expression for the data in terms of the unknown object susceptibility. The raw data acquired in the instrument in accordance with the present invention are the outputs of the focal plane array. The illumination is assumed to be quasimonochromatic with tunable central frequency, $\omega$, so that the data are proportional to the spectral density on the focal plane array and are acquired serially for multiple values of ω.

The relationship between the spectral density measured on the focal plane of the instrument and the susceptibility of the object is derived below. The measured optical intensity I(r, ω) is given by the spectral density—the ensemble average of the square magnitude of the incident field in the frequency domain at a single point, i.e., $$I(r,\omega) = \langle E^*(r,\omega)E(r,\omega)\rangle, \qquad (1)$$

with the brackets, $\langle\ \rangle$, denoting ensemble average.

From FIG. 1 it can be seen that the data are collected on a plane, with two-dimensional position given by ρ. The detected field is the superposition of a reference field $E_r$ and a field $E_s$ that is backscattered from the sample. As a result, the detected spectral density of Eq. 1 can be expressed as, $$I(\rho, k) = \langle |E_r(\rho, k) + E_s(\rho, k)|^2\rangle, \qquad (2)$$
$$= \langle |E_r(\rho, k)|^2 + 2\mathrm{Re}\{E_r^*(\rho, k)E_s(\rho, k)\} + |E_s(\rho, k)|^2\rangle,$$

where k=ω/c in free space. More complicated dispersion relations for k(ω) may also be employed for propagation in dispersive mediavas discussed in Marks et al., "A digital algorithm for dispersion correction in optical coherence tomography for homogeneous and stratified media," *Appl. Opt.*, vol. 42, pp. 204-17, (2003), which is incorporated herein by reference.

The function I(ρ, k) may be seen to be the sum of three terms: a background term independent of the object; an autocorrelation term that is second-order in the scattered field; and the real part of the desired signal S, where $$S(\rho,k) = \langle E^*_r(\rho,k)E_s(\rho,k)\rangle, \qquad (3)$$

It is assumed that the background term, for the assumed form of the incident field, is independent of ρ and may be subtracted in a calibration stage. The autocorrelation term is neglected because the object is assumed to be weakly scattering. Davis et al., "Autocorrelation artifacts in optical coherence tomography and interferometric synthetic aperture microscopy," *Opt. Lett.*, vol. 32, pp. 1441-43, (2007) (hereinafter, Davis (2007)) provides a discussion of the performance of ISAM in relation to the autocorrelation artifact, and is incorporated herein by reference. The remaining term is proportional to the real part of the desired signal S.

From Eq. 3 it can be seen that the signal S is a cross correlation function. Taking the Fourier transform with respect to k allows this correlation to be expressed in the spatial domain as, $$\hat{S}(\rho,\Delta z) = \langle \hat{E}_r^*(\rho, z - \Delta z)\hat{E}_s(\rho, z)\rangle, \qquad (4)$$

The optical path in the reference arm of the instrument can be set so that, $$\hat{S}(\rho,\Delta z) = 0, \forall \Delta z < 0. \qquad (5)$$

This condition corresponds to an optical path in the reference arm that is shorter than the minimum optical path in the sample arm by at least the reciprocal of the source bandwidth (in wavenumbers). The condition on $\hat{S}$ given in Eq. 5 ensures that the real and imaginary parts of S are related by a Hilbert transform. As a result, the imaginary part of the data S can be calculated from the real part, as discussed by Davis (2007).

The observable quantity S must be related to the object, illumination source and instrumentation to complete the forward model. To do this it is necessary to define the reference field $E_r$ and the scattered field $E_s$ seen in Eq. 3.

Let the field at the source field plane of FIG. 1 be given by $E_0(\rho,k)$. Note that the transverse position ρ is used to describe positions on the source plane and on the detector plane, as the former is imaged on to the latter. The field incident on the object is then given by $$E_i(r,k) = \int d^2\rho E_0(\rho,k)G_{i0}(r_\|, \rho; z, k), \qquad (6)$$

where r is the position in the object, $r_\|$ is the transverse component of r, z is the component of r orthogonal to $r_\|$ and $G_{i0}$ is the Green's function describing propagation of light with wavenumber k from the source plane to the transverse plane at z.

Scattering from the object is governed by the susceptibility η, which is assumed to be independent of the wavenumber k over the bandwidth of the system. Scattering is treated within the first Born approximation. As a result, a scattered field $k^2\eta(r)E_i(r,k)$ is produced within the object. This field propagates back through the instrument to give the field $E_s$ at the detector. This field is therefore $$E_s(\rho, k) = \int d^3r [k^2\eta(r)E_i(r, k)]G_{0i}(\rho, r_\|; z, k) \qquad (7)$$
$$= k^2 \int d^3r \int d^2\rho' E_0(\rho', k)G_{i0}(r_\|, \rho'; z, k)G_{0i}(\rho, r_\|; z, k)\eta(r),$$

where $G_{0i}$ describes propagation from the z plane in the object to the detector plane. This propagation operation to position ρ on the detector plane is equivalent to propagation to the position ρ on the source plane.

By reciprocity, $G_{0i}$ and $G_{i0}$ are related via $$G_{0i}(\rho,r_\|;z,k) = G_{i0}(r_\|, \rho;z,k). \qquad (8)$$

In this regard, one may refer to Potton, "Reciprocity in optics," *Rep. Prog. Phys.*, vol. 67, pp. 717-54, (2004), which is incorporated herein by reference. Furthermore, the mapping of the source into the sample will be assumed to be shift invariant across the relevant field of view, so that $$G_{i0}(r_\|, \rho; z, k) = g\left(r_\| - \frac{\rho}{M}; z, k\right), \qquad (9)$$

where M is the magnification of the telescope and g is the normalized-unit point spread function (PSF) for illumination to plane z at wavenumber k. The telecentric optics in the sample arm ensure that the magnification M is not a function of z.

Substituting Eqs. 8 and 9 into Eq. 7 results in $$E_s(\rho, k) = \qquad (10)$$
$$k^2 \int d^3r \int d^2\rho' E_0(\rho', k)g\left(r_\| - \frac{\rho'}{M}; z, k\right)g\left(r_\| - \frac{\rho}{M}; z, k\right)\eta(r).$$

Returning to the definition of S (Eq. 3), it can be seen that the data are the correlations between the backscattered field and the reference field. The reference field is an image of the source, as seen in FIG. 1. It will be assumed that the pupil used in the telecentric sample-arm telescope results in a significantly lower resolution than achieved in the reference arm. This leads to the approximation $$S(\rho, k) = \langle E_r^*(\rho, k) E_s(\rho, k) \rangle, \quad (11)$$
$$\approx \langle E_0^*(\rho, k) E_s(\rho, k) \rangle.$$

Substituting into Eq. 10, $$S(\rho, k) = \frac{k^2}{M^2} \int d^3 r \int d^2 \rho' W\left(\frac{\rho'}{M}, \frac{\rho}{M}; k\right) g\left(r_\| - \frac{\rho'}{M}; z, k\right) g\left(r_\| - \frac{\rho}{M}; z, k\right) \eta(r), \quad (12)$$

where W is the demagnified cross-spectral density $$W(\rho', \rho; k) = M^2 \langle E^*_0(M\rho, k) E_0(M\rho', k) \rangle. \quad (13)$$

It will be assumed that the coherence of the source field is spatially invariant and that the intensity of the illuminating field $E_i$ is constant over the extent of the object. These assumptions allow the cross-spectral density to be expressed as a homogeneous Schell-model source (see Mandel and Wolf, (1995):

$$W(\rho', \rho; k) = A(k) b(\rho' - \rho; k). \quad (14)$$

Equation 14 can be used to simplify the expression for the data seen in Eq. 12. Denoting convolution over the transverse axes by *, and separating the three-dimensional position r into transverse and axial components $r_\|$ and z, $$S(\rho, k) = \quad (15)$$
$$k^2 A(k) \int dz \int d^2 r_\| [b*g]\left(r_\| - \frac{\rho'}{M}; z, k\right) g\left(r_\| - \frac{\rho}{M}; z, k\right) \eta(r_\|; z).$$

The second integral above can also be recognized as a two-dimensional convolution, giving $$S(\rho, k) = \int dz [h*\eta]\left(\frac{\rho}{M}; z; k\right), \quad (16)$$

where $$h(-r_\|; z, k) = k^2 A(k) [b*g](r_\|; z, k) g(r_\|; z, k). \quad (17)$$

Equations 16 and 17 show that each transverse plane affects the data via a different PSF. The PSF for each plane is determined by the focusing optics (through g) and the source coherence properties (through b). In Eq. 17, the factor b*g can be identified with the illuminating field and the factor g can be associated with detection of the scattered light.

The function g represents the field produced in the sample for a point source at the origin of the source plane. Thus the PSFs at different transverse planes are related by the laws of electromagnetic propagation. A field propagating in a homogenous medium can be expressed in an angular spectrum decomposition, as shown by Wolf, "Electromagnetic diffraction in optical systems. I. An integral representation of the image field," *Proc. R. Soc. London, Ser A*, 253, pp. 349-357, (1959), which is incorporated herein by reference.

$$g(r_\|; z, k) = -\frac{i}{2\pi} \int d^2 q \frac{G(q/k)}{k_z(q)} e^{i[q \cdot r_\| + k_z(q)z]}, \quad (18)$$

where $$k_z(q) = \sqrt{k^2 - q^2}, \quad (19)$$

and z=0 is the focal plane. That the angular spectrum G is a function only of q/k reflects an assumption of achromatic focusing. Note that the following analysis could easily be generalized to include chromatic optics.

Expressing the forward model in the Fourier domain is useful in the derivation of the ISAM data processing. From Eqs. 18 it can be seen that the two-dimensional Fourier transform of g is $$\tilde{g}(q; z, k) = -2\pi i \frac{G(q/k)}{k_z(q)} e^{ik_z(q)z}. \quad (20)$$

The transfer function $\tilde{h}$ can then be found as the Fourier transform of Eq. 17, $$\tilde{h}(-q; z, k) = \quad (21)$$
$$-4\pi^2 k^2 A(k) \int d^2 q' B(q'; k) \frac{G(q'/k)}{k_z(q')} \frac{G[(q-q')/k]}{k_z(q-q')} e^{i[k_z(q') + k_z(q-q')]z},$$

where B(q;k) is the Fourier transform of b(ρ; k).

This transfer function $\tilde{h}$ can be used to take Eq. 16 into the Fourier domain $$\tilde{S}(-q; k) = \quad (22)$$
$$-4\pi^2 k^2 M^2 A(k) \int dz \int d^2 q' B(q'; k) \frac{G(q'/k) G[(Mq-q')/k]}{k_z(q') k_z(Mq-q')} \times$$
$$\tilde{\eta}(-Mq; z) e^{i[k_z(q') + k_z(Mq-q')]z}.$$

The exponential factor can be regarded as a Fourier kernel giving, $$\tilde{S}(-q; k) = \quad (23)$$
$$-4\pi^2 k^2 M^2 A(k) \int d^2 q' B(q'; k) \frac{G(q'/k) G[(Mq-q')/k]}{k_z(q') k_z(Mq-q')} \times \tilde{\eta}$$
$$\{-Mq; -[k_z(q') + k_z(Mq-q')]\},$$

where $\tilde{\eta}$ is the three-dimensional Fourier transform of the susceptibility. Equation 23 represents the most general Fourier-domain model for the partially-coherent ISAM system.

Coherent Illumination

A limiting illumination case occurs when the source field is fully coherent. This can be achieved my reducing the iris in FIG. 1 to a point-like aperture, giving a fully coherent plane wave at the source field plane. The case of full-field plane-wave illumination was considered in Marks (2007) and can be recovered here by setting $W(\rho, \rho', k) = k^2 A(k)$, i.e., full spatial coherence. This gives $B(q; k) = 4\pi^2 \delta(q/k)$ and Eq. 21 reduces to $$\tilde{h}(-q; z, k) = -16\pi^4 k^2 A(k) \frac{G(0)}{k} \frac{G[q/k]}{k_z(q)} e^{i[k+k_z(q)]z}. \quad (24)$$

The Fourier-domain forward model is then (c.f. Eq. 23), $$\tilde{S}(-q; k) = -16\pi^4 k M^2 A(k) G(0) \frac{G(Mq/k)}{k_z(Mq)} \tilde{\eta}\{-Mq; -[k+k_z(Mq)]\}. \quad (25)$$

This equation is the same as the result of Marks (2007) (Eq. 6 in that work) up to constant prefactors. The prefactors differ due to small differences in the definitions of the physical properties of the system.

Incoherent Illumination

The other limiting-case source statistics are achieved for an incoherent source. In this case no two points on the source plane are correlated, giving $W(\rho, \rho', k) = k^2 A(k) \delta[k(\rho'-\rho)]$, and hence $B(q; k) = 1$. An incoherent source can be realized by opening the iris seen in FIG. 1 very wide.

For an incoherent source, the transfer function of Eq. 21 becomes $$\tilde{h}(-q; z, k) = \quad (26)$$
$$-4\pi^2 k^2 A(k) \int d^2 q' \frac{G(q'/k)}{k_z(q')} \frac{G[(q-q')/k]}{k_z(q-q')} e^{i[k_z(q')+k_z(q-q')]z}.$$

The equation above is identical to the transfer function describing a single-objective confocal scanned-beam OCT system (see Eq. 29 in Davis et al., "Nonparaxial vector-field modeling of optical coherence tomography and interferometric synthetic aperture microscopy," *J. Opt. Soc. Am. A*, 24, pp. 2527-42, (2007), hereinafter "Davis (2007a)", incorporated herein by reference). This equivalence can be physically justified. In the case of scanned-beam OCT, a focused beam is scanned transversely through the sample. Data measured at each transverse position of the beam are taken at different times, so that there is no interference between the fields produced for different scan positions. In the case of incoherent illumination, the illuminating field may be considered to consist of a superposition of mutually incoherent beams distributed in the transverse direction, each of which is analogous to a transverse position of the beam in the scanned-beam case. While the component beams all illuminate the object simultaneously, the light of one beam, scattered by the object, does not interfere with the light of other constituent beams. Therefore, while the scattered fields from many component beams overlap on the focal plane array, they do not interfere, and act as if each beam illuminated the object sequentually, rather than simultaneously. The same data may be recorded by replacing the incoherent source with a transversely scanned beam with the same spot size as that of the component beams of the incoherent illumination.

The results discussed above demonstrate that, by controlling source coherence, the full-field instrument may produce data similar to those that can be acquired with the scanned-beam implementations, but in a highly parallel fashion. It is important to note that even absent the solution of the inverse problem, the result is of considerable import for wide-field OCT because it provides a means to mitigate cross-talk artifacts that limit the utility of that modality. This point is expanded upon below under the heading "Multiple Scattering."

Approximate Models and Inverse Scattering

The central enabling concept behind ISAM technology is the application of inverse scattering algorithms to the collected data. The benefit of applying inverse scattering algorithms is that regions that are regarded as out of focus in OCT are brought into diffraction-limited resolution. In both the full-field case of Marks (2007) and the confocal case of Davis (2007a) and Ralston (2007), the inverse scattering algorithms reduce to linear filtering and Fourier resampling operations. The reduction to these simple procedures requires approximations to the forward model but allows real time implementation, as discussed by Ralston et al., "Real-time interferometric synthetic aperture microscopy," *Opt. Express*, 16, pp. 2555-69, (2008), which is incorporated herein by reference. Experimental and the computational studies of Davis (2007a) and Ralston (2007) have shown excellent imaging fidelity despite the use of approximations in the derivation of the ISAM inverse scattering algorithms.

As shown in the previous section, varying the source coherence in the partially-coherent ISAM system allows a transition from full-field to confocal operation. In this section the inverse scattering algorithms for partially-coherent ISAM will be derived. In one limit this inverse scattering is identical to the inverse scattering for the full-field system and in the other limit it reduces to the confocal ISAM inverse processing. The intermediate regime will also be examined, with the result that the ISAM Fourier domain resampling varies as a function of the source coherence.

As shown in Davis (2007a), the physical phenomena behind confocal ISAM are fundamentally different depending on whether the imaged region can be characterized as near the focal plane or far from the focal plane. Fortuitously, for a single-objective system the ISAM Fourier-domain resampling is the same in either case, meaning that the near-focus and far-from-focus inverse scattering algorithms are compatible. By contrast, the full-field ISAM inverse scattering of Marks (2007) has only a single region of operation but a Fourier resampling that is different from the confocal case. For partially-coherent illumination in the system illustrated in FIG. 1, there are again two regions of operation (as in the confocal case) but in this case the Fourier resampling schemes are not commensurate across the regions.

Both the near-focus and far-from-focus cases for partially-coherent ISAM are discussed below. However, the near-focus regime is emphasized in the present description for two reasons: first, the signal returned from the near-focus region is generally higher than from the out-of-focus region; and second, the source coherence can be adjusted so as to extend the near-focus region. The simulations shown below provide further justification for the use of near-focus inverse scattering.

Near-Focus Operation

The near-focus ISAM scattering model is found by applying a simplifying assumption to the transfer function of Eq. 21 in the limit of a slowly varying exponential factor. This exponential will be slowly varying for regions near the focal plane, as shown by Davis (*2007a*).

In order to apply the approximation, it is necessary to assume forms for B and G. Here it will be assumed that the pupil has a Gaussian distribution so that $$G(q/k) = \exp\left(-\frac{\alpha^2 q^2}{2k^2}\right), \quad (27)$$

where the parameter $\alpha=\sqrt{2}/\text{NA}$, and NA is the numerical aperture of the lens.

The coherence of the source is described by B which is of the form $$B(q;k) = \frac{1}{\chi}\frac{\alpha^2}{2\pi}\exp\left(-\frac{1-\chi}{\chi}\frac{\alpha^2 q^2}{2k^2}\right). \quad (28)$$

This form for B means that the coherence length on the source plane is $\sqrt{(1-\chi)/\chi}\, M\alpha/k$, i.e., the coherence length scales with the wavelength via the 1/k factor. This scaling property results in an angular divergence from the source that is independent of k, a fact evidenced by the dependence of B on q/k. For the case when $\chi=0$, $B(q;k)=\delta(q/k)$ and coherent illumination is described. When $\chi=1$, $B(q;k)=\alpha^2/(2\pi)=1/(\pi\text{NA}^2)$, describing aperture-area-normalized incoherent illumination. All intermediate values of $\chi$ describe a partially coherent source.

As described in Davis (2007a), the factor $B(q';k)G(q'/k)G[(q-q')/k]$ appearing in the integrand of $\tilde{h}$ (Eq. 21) will be peaked around some point p' in q' space. The remaining factors in Eq. 21 will be expanded in a Taylor series about p' and all but the leading term discarded. This results in $$\tilde{h}(-q;z,k) \approx \quad (29)$$
$$-4\pi^2 k^2 A(k)\frac{e^{i[k_z(p')+k_z(q-p')]z}}{k_z(p')k_z(q-p')}\int d^2q'\, B(q';k)G\left(\frac{q'}{k}\right)G\left(\frac{q-q'}{k}\right).$$

Given Eqs. 27 and 28 the integral above can be evaluated and the Taylor expansion point shown to be $p'=q\chi/(1+\chi)$. The transfer function then becomes $$\tilde{h}(-q;z,k) \approx -4\pi^2 k^2 A(k) \quad (30)$$
$$\frac{\exp\left\{i\left[k_z\left(\frac{q\chi}{1+\chi}\right)+k_z\left(\frac{q}{1+\chi}\right)\right]z\right\}}{k_z\left(\frac{q\chi}{1+\chi}\right)k_z\left(\frac{q}{1+\chi}\right)}\frac{k^2}{1+\chi}\exp\left(-\frac{\alpha^2 q^2}{2k^2(1+\chi)}\right).$$

From this expression and the forward model relation of Eq. 16, it can be seen that the Fourier domain forward model is $$S(-q;k)=C(q;k)\tilde{\eta}(-Mq;\beta(q;k)) \quad (31)$$

where $$C(q;k) = \frac{-4\pi^2 k^4 M^2 A(k)}{(1+\chi)k_z\left(\frac{Mq\chi}{1+\chi}\right)k_z\left(\frac{Mq}{1+\chi}\right)}\exp\left(-\frac{\alpha^2 Mq^2}{2k^2(1+\chi)}\right), \quad (32)$$

and $$\beta(q;k) = -k_z\left(\frac{Mq\chi}{1+\chi}\right)-k_z\left(\frac{Mq}{1+\chi}\right). \quad (33)$$

Figure 2:
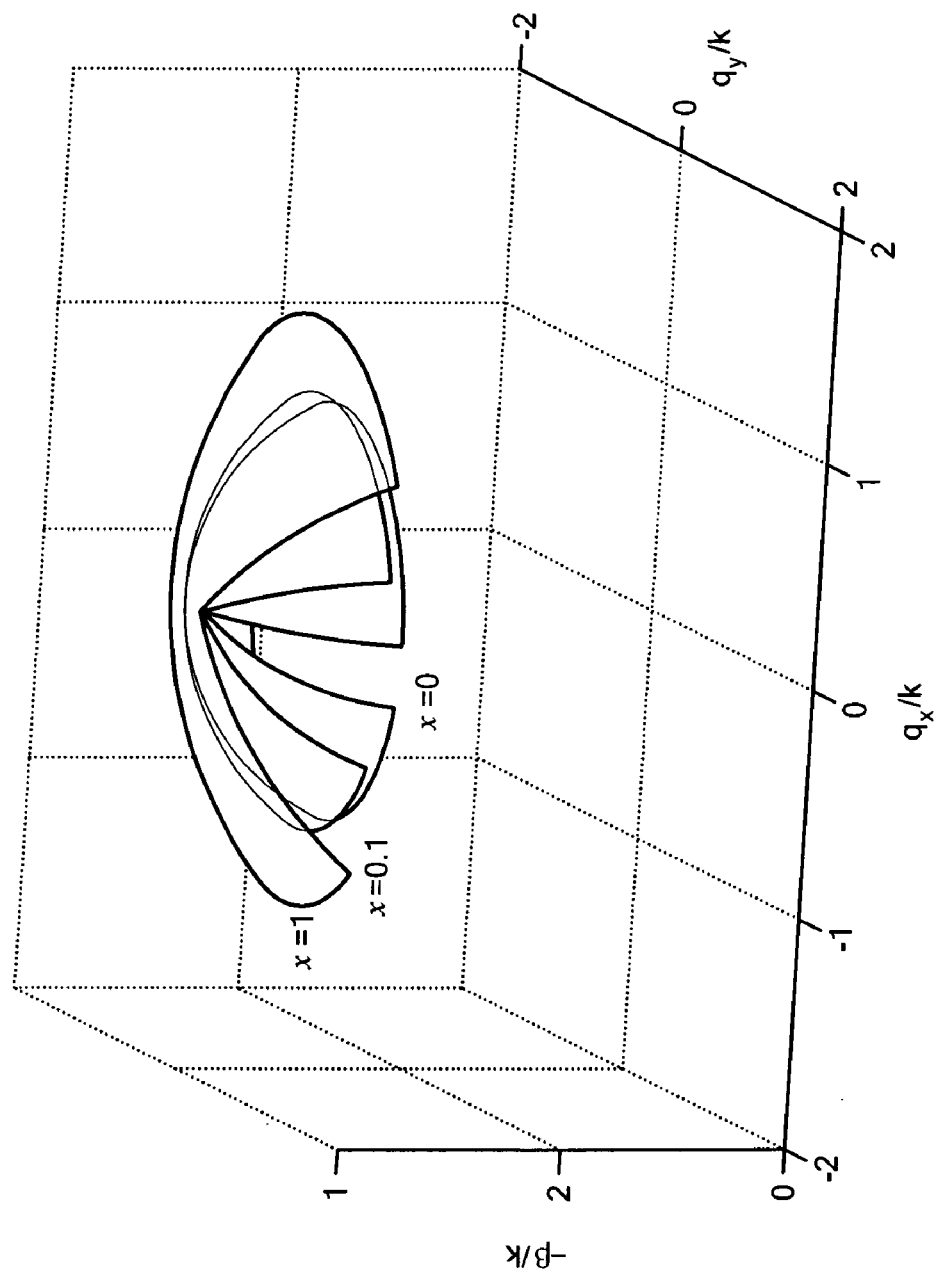
FIG. 2 shows contours of the mapping $\beta(q;k)$ for various coherence parameters $\chi$ and for unity wavenumber k.

The benefit of the approximation made in Eq. 29 is that the multiplex model of Eq. 23 is reduced to a one-to-one mapping between the object Fourier space and the data Fourier space, as seen in Eq. 31. That is, within the validity of the near-focus approximation, data collected at transverse Fourier component q and wavenumber k depend only on the three-dimensional Fourier transform of the object at $(Mq, -\beta)$. This relation is illustrated in FIG. 2, where the surfaces shown represent the locus of points in the Fourier-domain susceptibility that affect the data collected at wavenumber k.

Far-From-Focus Operation

The integral giving the transfer function h in Eq. 21 contains an exponential factor that will be rapidly oscillating over q', for large values of |kz|. Large values of |kz| describe regions away from the focus. For these far-from-focus regions the approximation of Eq. 29 is not appropriate, as the oscillatory exponential is not well represented by only the first term of its Taylor series.

As described in Davis (2007a), the stationary phase method (see Sec. 3.3 of Mandel (1995)) can be used to approximate $\tilde{h}$. The stationary point is the value of q' at which the gradient of the exponential argument is zero. Here the stationary point can be seen to be $q'=q/2$. This results in the far-from-focus approximation $$h(-q;z,k) \approx -4\pi^2 k^4 A(k)\frac{\pi i}{kz}e^{i2k_z(q/2)z}B\left(\frac{q}{2};k\right)G\left(\frac{q}{2k}\right)G\left(\frac{q}{2k}\right). \quad (34)$$

Thus the far-from-focus model can also be written in the form $$S(-q;k)=C'(q;k)\tilde{\eta}'(-Mq;\beta'(q;k)) \quad (35)$$

where $$\tilde{\eta}'(q,\beta) = \int dz\frac{\tilde{\eta}(q,z)}{kz}e^{-i\beta z}, \quad (36)$$

is the Fourier transform of an axially attenuated object, $$\beta'(q;k) = -2k_z\left(\frac{Mq}{2}\right), \quad (37)$$

and C' describes the system bandpass, which in this example is $$C'(q;k) = \frac{-i2\pi^2 k^2 M^2 \alpha^2 A(k)}{\chi}\exp\left(-\frac{\alpha^2 M(1+\chi)q^2}{8k^2\chi}\right). \quad (38)$$

This far-from-focus model has several significant differences when compared to the near-focus model of Eqs 31, 32 and 33. Equation 36 includes a linear attenuation given by the distance from focus. This describes a decrease in signal power for scatterers away from the focus. The resampling described in Eq. 37 differs from the near-focus of Eq. 33 in that it is not a function of the coherence parameter $\chi$. As described in Davis (2007a), the near- and far-from-focus forms of $\beta$ and $\beta'$ are equal in the confocal/incoherent case, meaning that the same ISAM resampling can be applied in either region. For $\chi\neq 1$ the expression the expressions for $\beta$ and $\beta'$ are not equal, suggesting the use of different inverse scattering procedures depending on whether a scatterer is near or far-from focus.

The Near- to Far-From-Focus Transition

For the full-field/coherent system, the near-focus approximation of the Near-Focus section above is exact, meaning that there is no far-from-focus regime. In the confocal/incoherent system the near- to far-from-focus transition occurs at one Rayleigh range, as shown in Davis (2007a), but the Fourier domain resampling in each region is equal. As discussed above, the behavior is more complicated for a partially coherent source, i.e., $0 \leq \chi \leq 1$.

The transition between the near- and far-from-focus regimes can be found by considering a point scatterer at the plane z. The expected data may be evaluated for both regimes and the signal strength compared. Using the results from the Near-Focus and Far-From-Focus sections above, it may be seen that the magnitudes of the signals are equal at the plane $$|z_t| = \frac{1+\chi}{2\chi} \frac{a^2}{k} = \frac{1+\chi}{2\chi} \frac{\lambda}{\pi NA^2}. \quad (39)$$

The factor $\lambda/(\pi NA^2)$ may be recognized as the Rayleigh range. Consistent with previous results, the transition plane $z_t$ may be seen to be one Rayleigh range for confocal/incoherent operation ($\chi=1$) and at infinity for full-field/coherent operation ($\chi=0$).

The Fourier-domain resampling ($\beta$ or $\beta'$) varies between near- and far-from-focus regimes. Here it is suggested that the near-focus expression of Eq. 33 can be used in most instances—for high-coherence sources the near-focus region is large, and for low-coherence sources Eq. 37 approximates Eq. 33. This claim will be revisited in the context of the numerical simulations discussed below.

Inverse Scattering

Given the approximated model of Eq. 31, ISAM inverse scattering can be easily described and applied in real time, in accordance with the discussion of Ralston (2008). The algorithm can be split into two distinct parts-filtering and resampling.

The filtering operation ameliorates the effects of noise and, as far as possible, undoes the effects of C in Eq. 31. The linear filtering operation can be realized by a Fourier domain multiplication with some function $C^+$, i.e., the processed data is $$S^+(-q,k) = C^+(q;k)S(-q,k). \quad (40)$$

This inversion filter is designed to undo the effects of C without introducing instabilities in the presence of noise. There are a variety of standard methods to define $C^+$, with perhaps the most famous being the Wiener filter discussed by Wiener, *Extrapolation, Interpolation, and Smoothing of Stationary Time Series*, (MIT Press, 1964), which is incorporated herein by reference. A simple version of the Wiener filter is $$C^+(q;k) = \frac{C^*(q;k)}{|C(q;k)|^2 + \gamma^2}, \quad (41)$$

where $\gamma$ is a regularization parameter used to limit the value of $C^+$ and thus provide stability in the presence of noise.

The resampling operation involves warping the processed data $S^+$ in Fourier space so as to undo the effects of the imaging system. In Eq. 31 it can be seen that the Fourier-domain data is proportional to the three-dimensional Fourier transform of the object defined on a distorted coordinate system. The distortion is given by Eq. 33 and is illustrated in FIG. 2. By applying a one-dimensional interpolation at each q point, the mapping given by $\beta$ can be undone. As seen in earlier work, this processing removes out-of-focus blurring.

In standard OCT the full $\beta$–k relation is not used to reconstruct the data. Rather, a scaled axial Fourier transform is used to take spectral-domain OCT data into the spatial domain. This operation is equivalent to $\beta(q;k) = -2k$, a poor approximation to Eq. 33.

Multiple Scattering

Figure 3:
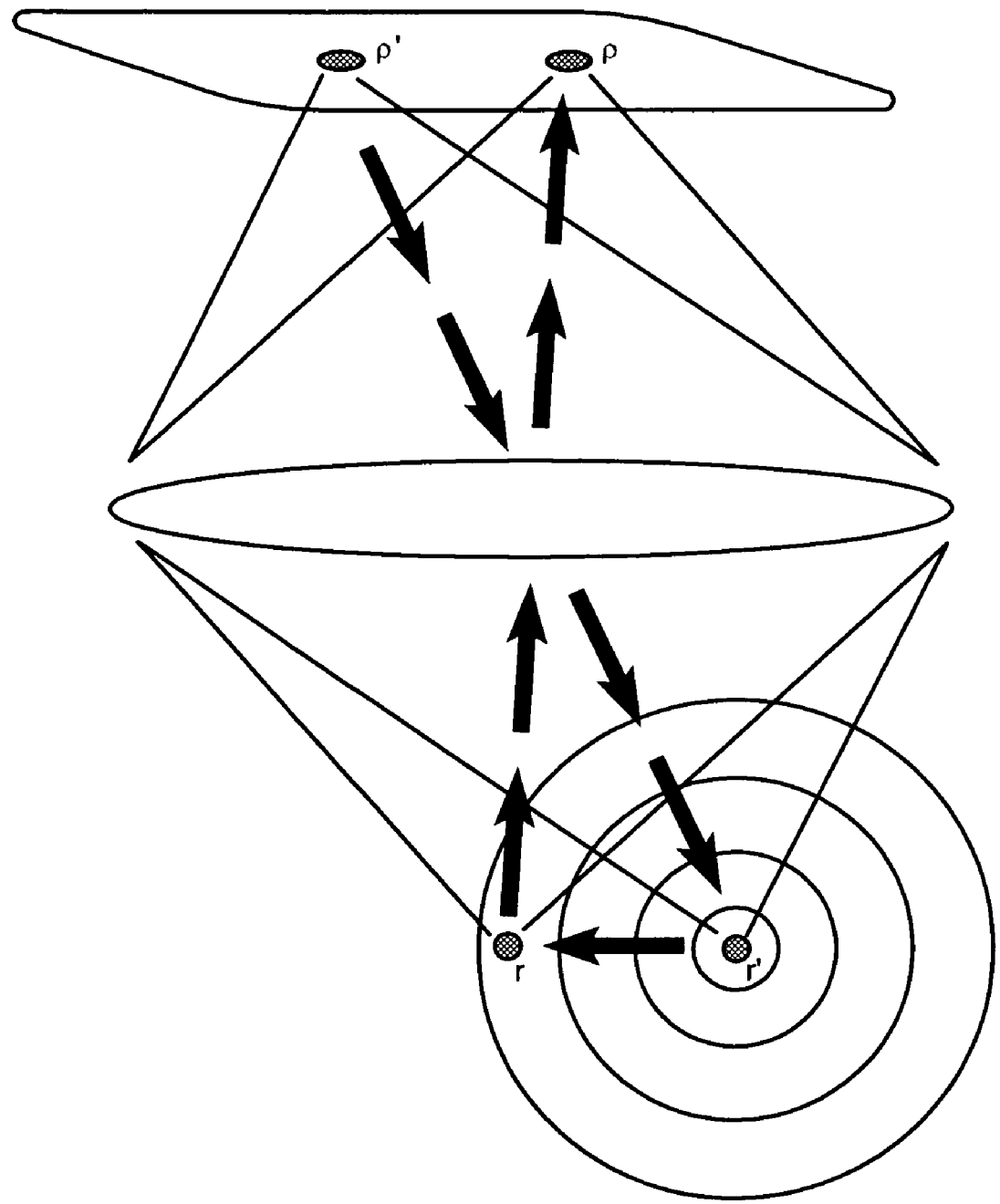
FIG. 3 illustrates multiple scattering—in this case, second-order scattering. Light from the source plane is focused into the sample, scatters twice and is focused onto the detector.

In both OCT and ISAM data are processed under the assumption that only singly-scattered light is present in the interferometric signal. As a result, any multiply-scattered light appearing in the interferogram is a source of error. In confocal systems, much of the multiply-scattered light is rejected at the confocal pinhole. Multiple scattering in a full-field system is illustrated in FIG. 3. In general, multiple scattering is more problematic in full-field systems, where more multiply-scattered light reaches a detector element. This section describes how partial coherence of the source can be used to mitigate the effects of multiple scattering.

As illustrated in FIG. 3, second-order scattering occurs when light from source position p' scatters from a position r' in the sample. This scattered light is scattered for a second time at r and subsequently propagates to the detector position ρ. This process can be described mathematically in the same way that first-order scattering was described in the General Case section above. The source field $E_0$ is propagated into the sample by $G_{i0}$, it scatterers in the object and is propagated using the free-space Green's function $G_f$. A second scattering event occurs in the object and propagation to the detector is given by $G_{0i}$. The scattered field $E_s$ at the detector is found by integrating over all source positions, and pairs of scattering locations, so that $$E_s(\rho,k) = k^4 \int d^3 r \int d^3 r' \int d^2 \rho' E_0(\rho',k) G_{i0}(r'_\shortparallel,\rho';z',k)\eta(r')G_f \\ (r,r';k)\eta(r)G_{0i}(\rho,r_\shortparallel;z,k). \quad (42)$$

This expression can be compared to the field due to single scattering seen in Eq. 7.

The free-space Green's function (see, e.g., Mandel (1995), Sec. 3.2.4) is $$G_f(r,r';k) = \frac{\exp(ik|r-r'|)}{|r-r'|}. \quad (43)$$

Using this expression and Eqs. 8, 9, 11 and 13, Eq. 42 becomes $$S(\rho,k) = \frac{k^4}{M^2} \int d^3 r \int d^3 r' \int d^2 \rho' W\left(\frac{\rho'}{M},\frac{\rho}{M};k\right) \times g\left(r'_\shortparallel - \frac{\rho'}{M};z',k\right) \quad (44) \\ \frac{\exp(ik|r-r'|)}{|r-r'|} g\left(r_\shortparallel - \frac{\rho}{M};z',k\right)\eta(r)\eta(r').$$

This expression represents the second-order scattering contribution to the collected data (c.f., the first order contribution given by Eq. 12.)

To see how the partial coherence of the source field can be used to mitigate multiple scattering effects, consider an object with strong scattering centers around $r^{(1)} = (R_\shortparallel^{(1)}, 0)$ and $r^{(2)} = (R_\shortparallel^{(2)}, 0)$. Since the focused field $g(r_\shortparallel; 0,k)$ is significant only in a small region around $r_\parallel=0$, multiple scattering from $r^{(1)}$ to $r^{(2)}$ will produce significant effects in the data only when $p' \approx MR_\parallel^{(1)}$ and $\rho \approx MR_\parallel^{(2)}$. This condition is illustrated in FIG. 3, where the scatterers lie in the focal regions corresponding to the points $\rho'$ and $\rho$ on the source/detector plane. When this condition is satisfied the $\eta(r)$, $\eta(r')$, $g(r'_\parallel - \rho'/M; z', k)$ and $g(r_\parallel - \rho/M; z, k)$ factors in Eq. 44 are simultaneously large around the volume of integration centered at $r'_\parallel = R_\parallel^{(1)}$ and $r_\parallel = R_\parallel^{(2)}$. The remaining factors in the integrand are the free-space Green's function and the cross-spectral density, which in the relevant region of the integration volume is approximately $W(R_\parallel^{(1)}, R_\parallel^{(2)}; k)$. For a fully coherent source this cross-spectral density is constant and does not have an effect. As the source coherence is reduced, $W(R_\parallel^{(1)}, R_\parallel^{(2)}; k)$ introduces attenuation to the multiple scattering contribution. As illustrated in FIG. 3, light from the source position $\rho'$ can be doubly-scattered primarily to the detector position $\rho$. If the source coherence length is less that $|\rho' - \rho|$, the interferometric visibility of the multiply-scattered light is low and hence gives minimal contribution to the data. This process is in contrast to single scattering, where the light originating from $\rho$ is primarily scattered to the vicinity of the same point $\rho$ on the detector.

Simulations

To demonstrate the accuracy of partially-coherent ISAM with regard to image reconstruction and rejection of multiple-scattering, numerical simulations are now presented. Synthetic single-scattering data are calculated by defining an object susceptibility $\eta$ and evaluating Eq. 12. In this case the object is defined to be three identical point scatterers. Second-order-scattering data from each pair of points is generated using Eq. 44. Higher-order scattering is assumed to produce negligible signal in the simulations presented here.

Data are collected at 50 values of k, evenly spaced around $k=2\pi/\lambda$ (where $\lambda$ is a fixed central wavelength) with a 25% bandwidth. The point scatterers in the object are located at $(20, 0, 0)\lambda$, $(0, 0, 15)\lambda$ and $(-20, 0, 30)\lambda$ in Cartesian coordinates, where $z=0$ is the focal plane. A numerical aperture of 0.2 is assumed and the detector is modeled as having x-y extent of $70\lambda \times 30\lambda$. Various values of the coherence parameter $\chi$ are simulated in order to demonstrate the effects of the partial coherence of the source.

Figure 4:
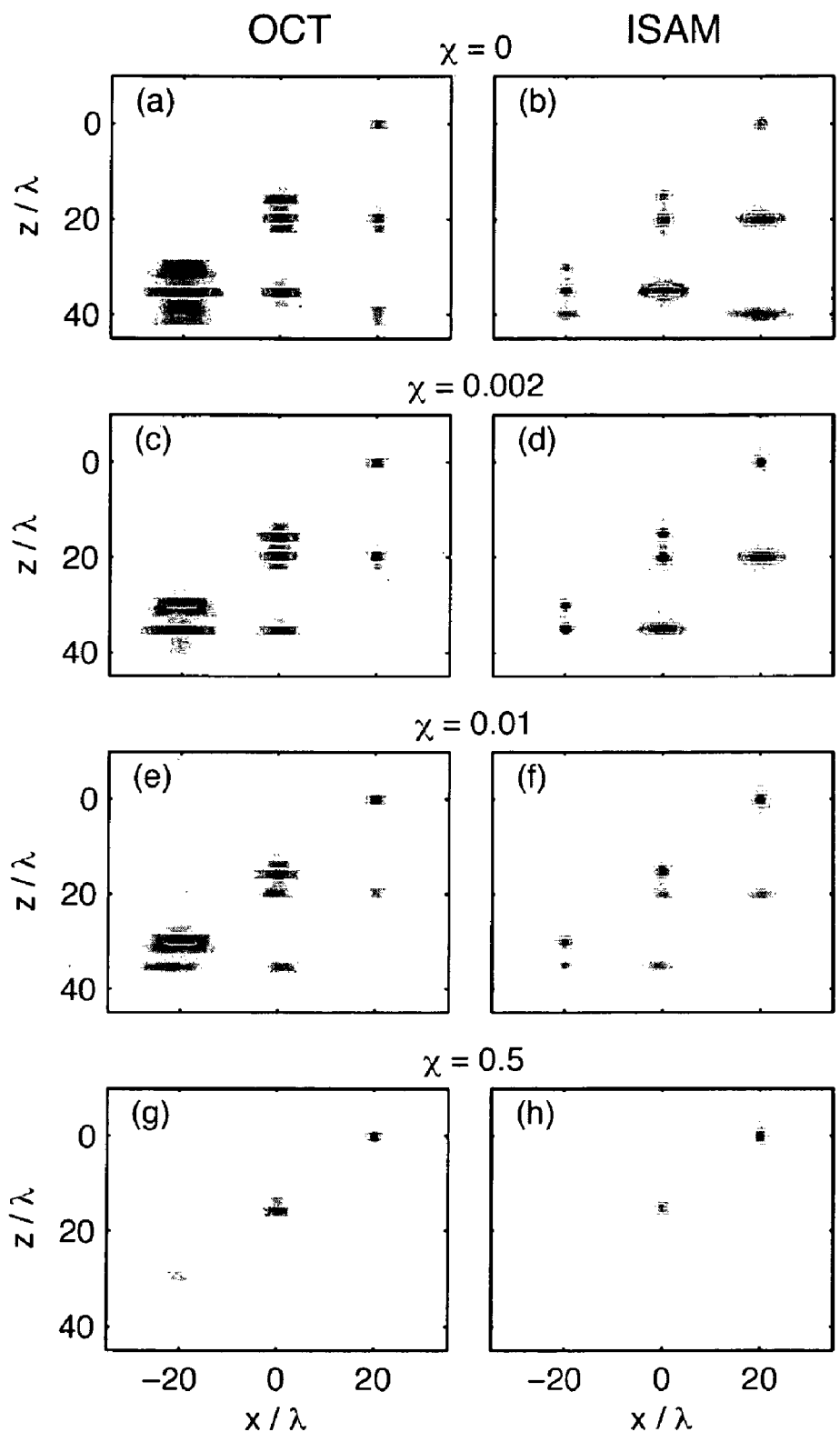
FIGS. 4a-h show results of simulation of ISAM imaging using partially coherent illumination in accordance with embodiments of the present invention. OCT (FIGS. 4a,c,e,g) and ISAM (FIGS. 4b,d,f,h) images are shown of an object consisting of three point scatterers. The source spatial coherence is varied as described by the parameter $\chi$. The coherence lengths are $\infty$(a,b) ($\chi$=0), 25$\lambda$ (c,d) ($\chi$=0.002), 11$\lambda$ (e,f) ($\chi$=0.01) and 1.1$\lambda$ (g,h) ($\chi$=0.5). The images are formed from data consisting of first- and second-order scattering effects. A projection over the y axis of the three dimensional image magnitudes is taken to produce the two-dimensional images displayed.

As described above, an OCT image can be recovered by taking a scaled axial Fourier transform of the data. ISAM reconstructions are found using the near-focus model described in the Near-Focus Operation section above, and the resampling approach described in the Inverse Scattering section. A linear filter (Eq. 40) was not applied in these examples, so as to allow a clear comparison between OCT images and the results of the novel ISAM resampling scheme. ISAM and OCT images can be seen in FIG. 4—OCT images are seen in the left column and ISAM reconstructions in the right column. The data and images are complex functions on $R^3$, so, to facilitate visualization, projections of the function magnitude over the y axis are shown.

The ideal reconstructed image would consist of three diffraction-limited spots at the locations of the point scatterers. The images of FIG. 4 contain structure, not diffraction-limited in all cases, at these locations, in addition to artifacts caused by multiple scattering. As the source coherence is decreased (i.e., as $\chi$ is increased) the effects of multiple scattering lessen, as expected. ISAM image reconstruction can be seen to result in sharp images of the point scatterers, at the correct locations.

The ISAM processing does not necessarily produce diffraction limited spots from the multiple scattering artifacts, as the phase structure on these artifacts does not match the single-scattering patterns that ISAM is predicated on. A similar effect appears in the autocorrelation artifact shown by Davis (2007), which ISAM is seen to blur.

As discussed in connection with all of the inverse scattering models explored above, the characteristics of the system differ depending on whether an imaged scatterer can be characterized as near-focus or far-from-focus. The transition point between these two regimes is described in Eq. 39 and depends on the coherence properties of the source and the focusing characteristics of the objective lens. For the examples shown in FIG. 4 the transition planes are $z_t=\infty$ (no far-from-focus region) for $\chi=0$, $z_t=2000\lambda$ for $\chi=0.002$, $z_t=400\lambda$ for $\chi=0.01$, and $z_t=12\lambda$ for $\chi=0.5$. The scatterer at $(-20, 0, 30)\lambda$ is therefore in the far-from-focus region for the $\chi=0.5$ images of FIG. 4(g) and FIG. 4(h). This claim is supported by the lower reconstruction amplitude observed for this scatterer and predicted in the far-from-focus regime by Eq. 36. The ISAM Fourier-domain mapping also changes from near- to far-from focus, meaning that the use of the near-focus resampling to generate FIG. 4(h) introduces an error. However, the far-from-focus scatterer is still reconstructed as point-like, meaning that the error has minimal effect in this example.

In most scenarios the focal plane of the system is set to lie within the area of interest. This would suggest the use of the near-focus ISAM model of the Near-Focus Operation section above. The source coherence can then be set to minimize multiple scatter artifacts while also giving a sufficiently large transition plane $z_t$ so as to capture the region of interest. Ensuring the near-focus region encompasses the area of interest means that the near-focus model can be used with confidence and that the $z^{-1}$ loss in signal associated with far-from-focus operation does not adversely affect the SNR. However there may be cases where it is desirable to have some, or all, of the object in the out-of-focus region. In this case the change in resampling schemes between near-focus and far-from-focus operation (see Eqs. 33 and 37) can be minimized by selecting a large value of $\chi$ and/or using a low numerical aperture.

Concluding Remarks

The foregoing description shows, in accordance with embodiments of the present invention, precisely how coherence properties of the source of illumination in ISAM can play an important and useful role in image reconstruction. In both ISAM and OCT, decreasing the spatial coherence of the source helps reject multiple scattering artifacts and can improve image quality. By varying the source coherence, the ISAM instrument of the present invention can behave as a full-field imaging system (full source coherence), as a parallelized confocal system (source incoherence) or in some intermediate regime (partial source coherence). The source coherence can be chosen by striking a balance between the competing goals of multiple scatter rejection (improves with decreasing coherence) and a large axial imaging range over which the signal strength does not decrease (improves with increasing coherence). This depth over which the signal strength is constant (given by Eq. 39) can be made many times larger than the Rayleigh range given a prudent choice of coherence properties. Unlike traditional OCT systems, which give diffraction-limited resolution over the Rayleigh range only, ISAM processing enables a diffraction limited image to be achieved over this whole constant-signal volume. Furthermore, the use of physics-based image reconstruction algorithms means that a quantitative estimate of the susceptibility is obtained.

The inverse scattering solution presented here compensates for whatever the spatial bandwidth of the partially coherent source is relative to the pupil bandpass of the system. Exact solutions to the inverse scattering problem that do not employ approximate solutions based on asymptotic methods are within the scope of the present invention, as are more general apertures than the Gaussian aperture that has been described as a heuristic convenience.

The present invention may be embodied in any number of instrument modalities. In alternative embodiments, the disclosed methods for inteferometric microscopy using partially coherent illumination may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product). These and other variations and modifications are within the scope of the present invention as defined in any appended claims.

We claim:

1. A method for determining a three-dimensional susceptibility of a sample, the method comprising:
   a. illuminating the sample with partially coherent light derived from a source;
   b. superposing scattered radiation from the sample with a reference beam derived from the source, using optics characterized by a focus and a Rayleigh range, to provide a detector signal at a detector, wherein the sample is disposed at a distance from the focus of the optics that exceeds the Rayleigh range;
   c. deriving a forward scattering model relating measured data to structure of an object; and
   d. solving an inverse scattering problem based upon the forward scattering model and the detector signal for a three-dimensional transform of the susceptibility, to derive a three-dimensional susceptibility of the sample from the transform of the susceptibility.

2. A method in accordance with claim 1, further comprising a step of varying the spatial coherence of the source.

3. A method in accordance with claim 1, further comprising a step of spectrally resolving the detected light.

4. A method in accordance with claim 1, wherein the step of solving the inverse scattering problem includes solving a least squares problem relative to a forward scattering model.

5. A computer program product for use on a computer system for determining a three-dimensional susceptibility of a sample, the computer program product comprising a computer usable medium having computer readable program code thereon, the computer readable program code including:
   a. program code for generating a forward scattering model based on forward scattering of partially coherent light by a point source;
   b. program code for receiving a signal based on coherent detection of scattering from the sample; and
   c. program code for solving, by means of resampling, an inverse scattering problem based upon the detector signal, thereby deriving a three-dimensional susceptibility of the sample based on comparing the detected signal to data predicted from the forward scattering model.

6. A method for determining a three-dimensional susceptibility of a sample, the method comprising:
   a. illuminating the sample with partially coherent light derived from a source;
   b. superposing scattered radiation from the sample with a reference beam derived from the source, using optics characterized by a focus and a Rayleigh range, to provide a detector signal at a detector;
   c. deriving a forward scattering model relating measured data to structure of an object; and
   d. solving an inverse scattering problem by means of resampling, based upon the forward scattering model and the detector signal for a three-dimensional transform of the susceptibility, to derive a three-dimensional susceptibility of the sample from the transform of the susceptibility.

7. A method in accordance with claim 6, further comprising a step of varying the spatial coherence of the source.

8. A method in accordance with claim 6, further comprising a step of disposing the sample at a distance from the focus that exceeds the Rayleigh range.

9. A method in accordance with claim 6, further comprising a step of spectrally resolving the detected light.

10. A method in accordance with claim 6, wherein the step of solving the inverse scattering problem includes solving a least squares problem relative to a forward scattering model.

* * * * *